United States Patent [19]

Harner

[11] Patent Number: 5,479,941
[45] Date of Patent: Jan. 2, 1996

[54] DEVICE FOR INDUCING ALTERED STATES OF CONSCIOUSNESS

[75] Inventor: Michael Harner, Norwalk, Conn.

[73] Assignee: Foundation of Shamanic Studies, Norwalk, Conn.

[21] Appl. No.: 138,343

[22] Filed: Oct. 18, 1993

[51] Int. Cl.⁶ .............................. A61G 15/00; A61G 7/04
[52] U.S. Cl. .............................................. 128/845; 5/616
[58] Field of Search ...................... 128/845, 846; 606/237, 239, 240, 241, 242, 245; 5/600, 601, 613; 297/DIG. 10

[56] References Cited

U.S. PATENT DOCUMENTS

| | | |
|---|---|---|
| 715,668 | 12/1902 | Kiddie . |
| 1,044,391 | 11/1912 | Jones ............................................ 472/2 |
| 1,106,255 | 8/1914 | Thompson . |
| 1,553,528 | 9/1925 | Hartong . |
| 2,671,898 | 3/1954 | Wada ...................................... 128/858 |
| 2,869,538 | 1/1959 | Hawk . |
| 3,558,129 | 1/1971 | Curry . |
| 3,646,896 | 3/1972 | Derujinsky . |
| 4,101,165 | 7/1978 | Hammer .................................. 297/273 |
| 4,379,588 | 4/1983 | Speice . |
| 4,544,202 | 10/1985 | Keaton . |
| 4,597,119 | 7/1986 | Padgett . |
| 4,720,140 | 1/1988 | Change, III . |
| 4,841,165 | 6/1989 | Bowles .................................... 307/132 |
| 4,862,530 | 9/1989 | Chen .......................................... 5/616 |
| 4,934,997 | 6/1990 | Skakas . |
| 5,044,377 | 9/1991 | Stillman ................................. 128/845 |
| 5,072,462 | 12/1991 | Attison ...................................... 5/600 |
| 5,078,451 | 1/1992 | Sobel . |
| 5,095,561 | 3/1992 | Green .......................................... 5/161 |

OTHER PUBLICATIONS

Eliade, M. (1964) in "Shamanism, Archaic Techniques of Ecstasy", (Panther Books) p. 130.
F. Andres (1939), "Die Himmelsreise der Caraibischen Medizinmanner", ZE, LXX, 3–5, p. 340.
Metraux (1944), "Le Shamanisme chez les Indiens de l'Amerique du Sud Tropicale", p. 208.
H. Kalweit (1988), "Dreamtime and Inner Space, The World of the Shaman", Shambhala Press, pp. 163–165.
Carlos Castaneda (1981), in "The Eagle's Gift," Washington Square Press, New York, N.Y., at pp. 61–62.
Bridwell et al. (1990), "Climbing Big Walls," pp. 58–59.

Primary Examiner—Michael A. Brown
Attorney, Agent, or Firm—Greenlee and Winner

[57] ABSTRACT

A rotating device for producing altered states of consciousness in a subject is provided. The subject's body rotates about a point in the center of the body support means at a speed between about 10 and about 60 revolutions per minute. In a preferred embodiment the direction of rotation is periodically reversed.

19 Claims, 4 Drawing Sheets

DEVICE FOR INDUCING ALTERED STATES OF CONSCIOUSNESS

FIELD OF THE INVENTION

This invention is a device for producing altered states of consciousness and comprises means for rotating the subject's body.

BACKGROUND OF THE INVENTION

Shamans in all cultures from ancient times until the present have employed means for altering their states of consciousness so as to induce visions and become conscious of non-ordinary realities where information helpful in healing illnesses and performing divinations may be available. Such means include the ingestion of psychotropic plant substances, the use of rhythmic and monotonous sound such as drumming and chanting, and dancing such as the Sufi whirling dervish dances.

Mircea Eliade (1964) in "Shamanism, Archaic Techniques of Ecstasy", (Panther Books) p.130 describes a practice of shamans of the Carib Indians of South America who place apprentices on "a platform suspended from the ceiling of the hut by a number of cords twisted together, which, as they unwind, make the platform revolve with increasing speed. The novice sings: 'The platform of the pujai will carry me to the sky . . .' and he enters the various celestial spheres one after the other and sees the spirits in a vision . . . Finally, the apprentice feels that he is carried into the sky and enjoys celestial visions." [Citing F. Andres (1939), "Die Himmelsreise der Caraibischen Medizinmanner" ZE LXX 3–5 p.340; and Metraux, "Le Shamanisme chez les Indiens de l'Amerique du Sud Tropicale", p.208.]

H. Kalweit (1988), "Dreamtime and Inner Space, The World of the Shaman", Shambhala Press, pp. 163–165 also describes this device and states that Robert Masters and Jean Houston have developed a similar device and found that a person being subjected to vertical or horizontal movements would, after about twenty minutes, experience an altered state of consciousness marked by highly realistic fantasies. The Masters and Houston device is described by its developers as similar to the European "witches' cradle", essentially a swing. Best results were achieved with the subject standing up with the eyes covered. A similar device was displayed at Essalen Institute in California during the 1960's, comprising a swing in which the subject could sit and swing and spin. The subject's entire body was covered and bound in canvas.

In none of these devices were means provided for controlling the speed of rotation or continuing the rotation over a period of up to thirty minutes with periodic reversal of the direction of rotation.

Carlos Castaneda (1981), in "The Eagle's Gift," Washington Square Press, New York, N.Y., at page 61–62 describes a harness device for a game in which the subject is suspended in a harness and must keep his balance as antagonists pull the ropes suspending the subject. The game is for sharpening visual prowess and gaining access to "memory of the body".

Devices which rotate the human body for purposes other than trance induction are known to the art. A number of such devices are designed for holding the subject in a seated rather than a reclining position, as shown in the following U.S. Patents: Kiddie U.S. Pat. No. 715,668 for "Pleasure Device" shows a swing which is hung on a rotatable mount to convert it into a carousel. Jones U.S. Pat. No. 1,044,391 for Roundabout Swing shows a rotating swing with a center post. A platform rotates about a shaft piercing its middle, suspending on ropes or wires which wind up around the shaft as the platform turns and cause reversal of its motion when unwinding. Curry U.S. Pat. No. 3,558,129 for "Children's Merry-Go-Round" shows a merry-go-round having retractable seat arms and powered by an electric motor. Keaton U.S. Pat. No. 4,544,202 shows a rotatable, manually powered lounge chair pivoted on a base. It has a gear connection to control the amount of rotation and to position the chair. Change U.S. Pat. No. 4,720,140 discloses a rotating platform for a sunbather having a chair mounted upon the platform. It has a center pivot about which the platform will rotate and the platform also has rollers at its end. The platform may be motor-powered. Sobel U.S. Pat. No. 5,078,451 discloses a manually rotatable chaise lounge in which the body support has a base element which is pivotally supported on the base frame. There are roller bearings between the base and the rotatable support.

U.S. Patents which disclose rotating display devices are as follows: Thompson U.S. Pat. No. 1,106,255 for Spectacular Display Apparatus shows a display device useful for stage productions with a sling for suspending the article to be displayed, such as a grand piano, which can be both rotated and moved vertically. The device may be rotated by pulling a rope attached to a pulley. Hartong U.S. Pat. No. 1,553,528 for "Display Device," shows a device for merchandise display having a circular platform rotated by means of an electric motor beneath the platform powering peripheral drive means.

Rotatable platforms on which sunbathers may lie supine are as follows: Derujinsky U.S. Pat. No. 3,646,896 for Sunbather's Rotatable Platform shows a sunbather's platform for two individuals who lie on it in a supine position. The platform is manually rotated. Speice U.S. Pat. No. 4,379,588 for Revolving Solar Lounger shows a chaise-type lounger which rotates on a base only in response to energization from the sun's rays. When the sun is covered by clouds, the lounge does not rotate. Padgett U.S. Pat. No. 4,597,119 for Suntanning Device, shows a rotatable sunbathing lounge which is pivotally supported on the pivot base and has an adjustable braking device to slow down the rotation to a desired speed, and is rotated by a spring or an electric motor, or gravity. This device is believed to provide rotational speeds considerably slower than required for trance induction.

A climber's device in which the subject may lie supine on a platform suspended on straps is the Portaledge by A-5 Company of Phoenix Ariz., depicted in Bridwell, et al. (1990), "Climbing Big Walls," pages 58–59. This device is not designed to rotate.

None of the foregoing disclose or suggest a rotating device upon which the subject may lie supine, suitable for trance induction. Nor has any rotating device been taught adapted to automatically rotate at a speed suitable for trance induction.

SUMMARY OF THE INVENTION

The device of this invention causes the occupant (called the "subject" herein) to enter a state of extreme relaxation in an altered state of consciousness which, in a darkened room or with the eyes closed or blindfolded, leads to an experience of weightlessness as though flying through space, stimulating dream-like imagery and out-of-body sensations. The device greatly enhances the subject's ability to enter the "shamanic state of consciousness" and experience the shamanic journey as part of the discipline of practical shamanism. For information on practical shamanism and shamanic journeying, see M. Harner (1980), "The Way of the Shaman," Harper and Rowe, San Francisco, Calif.

The device of this invention for inducing an altered state of consciousness comprises:

(a) body support not comprising a shaft extending upward from the center thereof means for supporting an adult human body preferably in a supine position;

(b) rotating means operably connected to said body support means to horizontally rotate said body support means, whereby the subject's body rotates about a point in the center of the body support means;

(c) speed control means operably connected to said rotating means to control the speed of said rotation to about 60 revolutions per minute.

In an alternative embodiment, the device of this invention comprises:

(a) body support means for supporting an adult human body preferably in a supine position;

(b) rotating means operably connected to said body support means to horizontally rotate said body support means at a speed between about 10 and about 60 revolutions per minute; and (c) means for reversing the direction of said rotation.

The term "altered state of consciousness" means a trance state, subjectively described as involving heightened stimulation of visions or out-of-body experiences; or an altered state objectively measured, e.g. as alteration of the normal waking beta-wave pattern of the brain to another pattern, such as alpha or theta waves. The device of this invention also induces relaxation and a sense of heightened well-being. Relaxation is helpful in the process of trance induction but is generally not in and of itself sufficient to induce an altered state of consciousness.

The term "body support means" includes any means known to the art including rigid platforms, preferably equipped with padding for the subject's comfort, hammocks, fabric supports attached to rigid frames, and the like.

The term "rotating means" includes any means known to the art for rotating the body support means. Motor-driven means are described in one preferred embodiment hereof. In another preferred embodiment manual rotation of a hanging platform causes a set of ropes or cords attached to the platform and by which it is suspended, to wind up, and also causes a separate rope or cord to wind around a circular spool or drum from which the set of ropes are suspended. Unwinding of the cords proceeds of its own accord until the set of ropes are unwound. The device then begins to wind up in the opposite direction by force of its own momentum. The separate rope proceeds from the spool through a pulley to hang at a convenient location to be pulled by an operator or the subject, to add extra energy to the system at the appropriate time and keep it from "running down." Spring means, gravity means such as a threaded shaft engaging with said body support means, magnetic means, sails affixed to the platform coupled with means for generating an airstream for filling the sails and rotating the platform, or other means known to the art are also comprised within the definition of "rotating means."

The body support means may be attached to an axle which is turned by an operator by means of ropes wound around it, or engaging with it in the manner of a fire stick rotated by a bowstring, or by treadle means powered by an operator as known to the art. In any such operator-powered means, the components should be sized and or geared or otherwise constructed so that the speed of rotation is at least 10 revolutions per minute and does not exceed 60 revolutions per minute. The rotating means may comprise a motor operably connected to a shaft affixed to the underside of said body support means, a motor operably connected to a shaft from which said body support means are suspended, or other configurations as will be readily appreciated by those skilled in the art. The rotation may be clockwise or counterclockwise, or preferably alternating in direction. It is preferred that the subject remain in a horizontal position.

The term "speed control means" comprises means known to the art for causing rotation at the desired speed, preferably excluding braking means which are undesirably inefficient for the present purposes. Such speed control means must ensure that the rotation does not exceed 60 revolutions per minute, as such speeds are likely to cause nausea and other undesirable side effects. Preferably the speed of rotation is between about 10 and about 60 revolutions per minute and more preferably is between about 15 and 30 revolutions per minute. Further, the speed control means preferably are automatic, i.e., they control the speed of rotation without intervention by the subject or an operator once the rotation has been started. In the case of devices powered by an operator, the speed control means will include sizing of the components and/or gear or cam arrangements such that the rotational speed of the body support means will not exceed 60 revolutions per minute no matter how much force is applied by the operator. For example, as will be apparent to those skilled in the art, where an operator pulls on a rope wound around an axle or drum, the axle or drum diameter and length of the rope can be adjusted to ensure speeds within the required range. A hanging platform which revolves by means of the unwinding of a set of ropes attached to its corners can be made to rotate more slowly when the overhead attachment point for the set of ropes is allowed to swivel more or less freely. Automatic speed control means may comprise a first sheave fixedly connected to a shaft which directly rotates said body support means, said first sheave being connected by means of a belt to a second sheave of a sufficiently smaller size to effect the preferred speed of rotation when said second sheave is connected to a standard DC motor. Preferably the motor is a reversing motor, capable of changing direction of rotation. Preferably, also a rheostat is operably connected to said motor to control the speed thereof.

The term, "means for reversing the direction of said rotation" may include any means known to the art such as the winding and unwinding of cords suspending the body support means, the use of a motor to wind such cords, or a reversing motor operably connected to actuation means, preferably programmably controlled. In one embodiment, the motor may be controlled to vary the rate of speed and the direction of rotation so that the body support means rotates in one direction for a period of time, slows, comes to a stop, then rotates in the opposite direction for a period of time. Preferably each period of rotation in one direction lasts at least about three minutes. Preferably, the platform reverses direction of rotation not more than once in three minutes and not less than once in 30 minutes. Such speed variation and direction reversing means include series of gears and cams operably connected to the motor to automatically slow and stop the rotation and reverse the direction of rotation one or more times during the period of operation of the device. Preferably, the motor is controlled via programmable control means, preferably connected to a rheostat and timer, to vary the speed and reverse the direction of rotation at specified intervals. Such programmable control means are known to the art and include programs embodied on computer chips. In one embodiment, the body support means is suspended on cords attached to a motor-powered winding mechanism connected to a timer. The motor is activated to wind the cords, thus rotating the body support means, and is timed to turn off after a sufficient number of revolutions such that the cords when released cause the body support means to rotate in the opposite direction at a slowly increasing speed not exceeding about 60 revolutions per minute, and preferably not exceeding about 30 revolutions per minute. The body support means comes to a stop when the cords are unwound and begins to turn in the opposite direction at a slowly increasing speed, and the motor is again activated to wind the cords up in the same direction as before. The cycle is repeated for as many times as desired. Hand-powered means such as a cord wound about a drum may be used instead of a motor to maintain the motion of revolution.

The device may also comprise timing means operably connected to said rotating means for timing the period of operation of said rotation, and stopping the rotation, such as by turning off the motor, at the end of the desired period of operation. A minimum period of at least about five minutes is required for effective induction of the altered state of consciousness, and it is desirable to provide the subject with a rotation period up to about thirty minutes, preferably about twenty minutes. Longer or shorter times may be used depending on the subject's susceptibility and tolerance. About five to about thirty minutes is adequate for most subjects.

The device may also be equipped with a shut-off button or other stopping means accessible to the subject allowing him to stop the device in case of emergency.

The device also preferably comprises light shield means for blocking light from the subject's eyes. The light shield may be anything known to the art to block light, such as a sleep mask, a scarf or bandanna, or other device. It is preferably attached to the device by a cord or chain so as to avoid loss. As will be appreciated by those skilled in the art, the support means may include a built-in helmet which functions as a light shield and also serves as a sound source for providing sounds to the subject to enhance induction of the altered state of consciousness. The sound source may comprise any means for producing sound known to the art, such as a speaker or speakers spaced around the device, or sounds produced by singing or instruments. Preferably wordless choral sounds are utilized as the sound source. It is most preferred that the sound source surround the subject. If speakers are used, four speakers spaced about the subject are preferred.

The entire system of a preferred embodiment comprises a rotating bed or platform capable of rotating horizontally about a center point, a light shield such as a blindfold, and a sound source, such as a speaker or set of speakers placed around the rotating device, all enclosed within a room which may be darkened as a substitute for, or in addition to, the wearing of the blindfold.

As will be appreciated by those skilled in the art, some of the above-described embodiments will produce a vertical component of motion up and/or down in addition to the horizontal rotation. If desired, the vertical component may be amplified, as in the case of gravity-powered threaded shafts, by lengthening the shaft, or in the case of hanging embodiments utilizing winding of ropes attached from the corners of the body-support means to a central point, by expedients such as increasing the diameter of the ropes, or by other means known to the art.

This invention also provides a method for inducing an altered state of consciousness comprising:

(a) sitting or lying horizontally supine on a body support means;

(b) activating rotating means to cause said body support means to rotate horizontally at a speed between about 10 and not exceeding about 60 revolutions per minute;

(c) maintaining said rotation for a period between about five and about thirty minutes.

It is preferred that the device be controlled by an automatic timer operably connected to said rotating means.

Also, in a preferred embodiment, the rotation accelerates, decelerates, comes to a stop, reverses direction, and again accelerates, decelerates, comes to a stop and reverses direction, repeating the cycle up to about 10 times in a 30-minute period. It is preferred that the motion be smooth rather than jerky, i.e. without deceleration during an acceleration period or vice versa.

As discussed above, if desired, a vertical component of motion may also be utilized.

Also, as discussed above, the method preferably also involves shielding light from the eyes. This may be done by the simple expedient of closing the eyes or operating the device in a darkened room, but is preferably done by using a light shield in the form of a blindfold which covers the eyes. It is preferable that as much light as possible be blocked from the subject's eyes so that complete or nearly complete darkness is experienced.

It is also preferred that the subject experience sounds to aid or enhance alteration of the state of consciousness. The sound may be provided by human singers or operators of musical instruments, or pre-recorded sounds may be used broadcast through a speaker or speakers, preferably at least four speakers surrounding the subject, preferably controlled by the same timing means controlling operation of the rotational device. Earphones connected to said body support means may also be employed, connected to a tape player or other sound generator. Wordless choral tones are preferred.

The method is preferably carried out using the devices of this invention described above, however, it will be appreciated by those skilled in the art that the device used may be simplified, for example by utilizing an operator to manually rotate a hanging platform or hammock-like device, or a platform mounted on a swivelling base. As described herein, it is preferred that the speed and direction of rotation of the device be automatically controlled; however it is possible to manually control these parameters, and excellent results may be achieved.

DETAILED DESCRIPTION OF THE PREFERRED EMBODIMENTS

Figure 1:
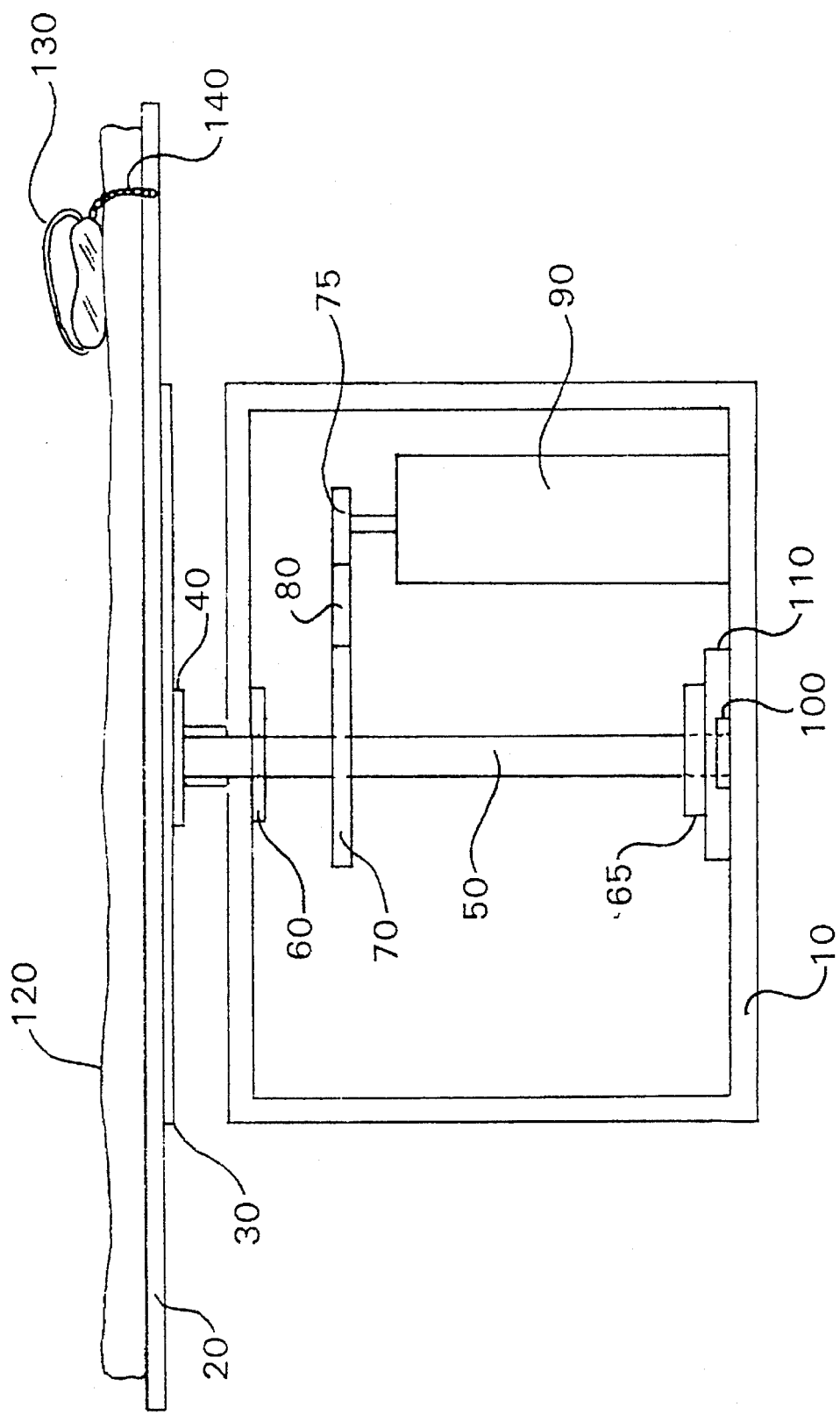
FIG. 1 is a diagram to scale of an embodiment of this invention providing a rotating platform powered by a central shaft attached to a motor.

Referring to FIG. 1, a non-bending platform 20 of a size suitable for supporting a mature adult human in a supine position is provided. In the embodiment depicted, the platform is 78 inches in length, however, it may be of any suitable length, preferably between about 66 inches and about 84 inches, and of any suitable width, preferably between about 18 inches and about 36 inches. The platform may be made of any rigid material such as wood or metal capable of supporting a human body. Padding, such as a foam pad 120 or air mattress, pads, blankets or pillows, may be placed atop the platform for the subject's comfort when resting on the platform.

Platform 20 rests on a support plate 30 made of a rigid material, preferably metal, and preferably circular in form, of sufficient size to provide a solid support for said platform. In a preferred embodiment, plate 30 is a ¼ inch thick, 32 inch-diameter circular aluminum plate. Plate 30 is fixedly attached to central shaft 50, preferably by means of a flange 40, depicted as a 6 inch aluminum flange bolted to platform 30, and fixedly attached to shaft 50. Shaft 50, preferably a 1 3/16 inch steel shaft, passes into case 10 which may be of any suitable material and shape to house the mechanism for rotating the platform, and is herein depicted as a 32 inch by 17 inch plywood box. The top of the case is fixedly attached to a first flanged bearing 60 through which the shaft 50 passes. A first sheave 70, preferably an 8 inch cast iron sheave, is fixedly attached to shaft 50 below flanged bearing 60. From thence shaft 50 passes downwardly through a second flanged bearing 65 fixedly attached to the bottom of the case, through a spacer such as wood block 110 and into another bearing 100 which it is turned to fit and which rests on the bottom of case 10.

The sheave 70 is connected via V-belt 80 to a second sheave 75 to provide a 2:1 reduction. Preferably second sheave 75 is a 4 inch diameter sheave. Second sheave 75 is attached to a motor 90, preferably a ⅓ horsepower DC permanent magnet motor, preferably bolted to the side of case 10 and blocked to rest on the bottom of case 10.

Further depicted in FIG. 1 is light shield 130 to be placed over the subject's eyes to block out as much light as possible to aid in trance induction. Light shield 130 may be attached to platform 20 by means of a cord or chain 140 so as to avoid it becoming lost or misplaced.

Figure 2:
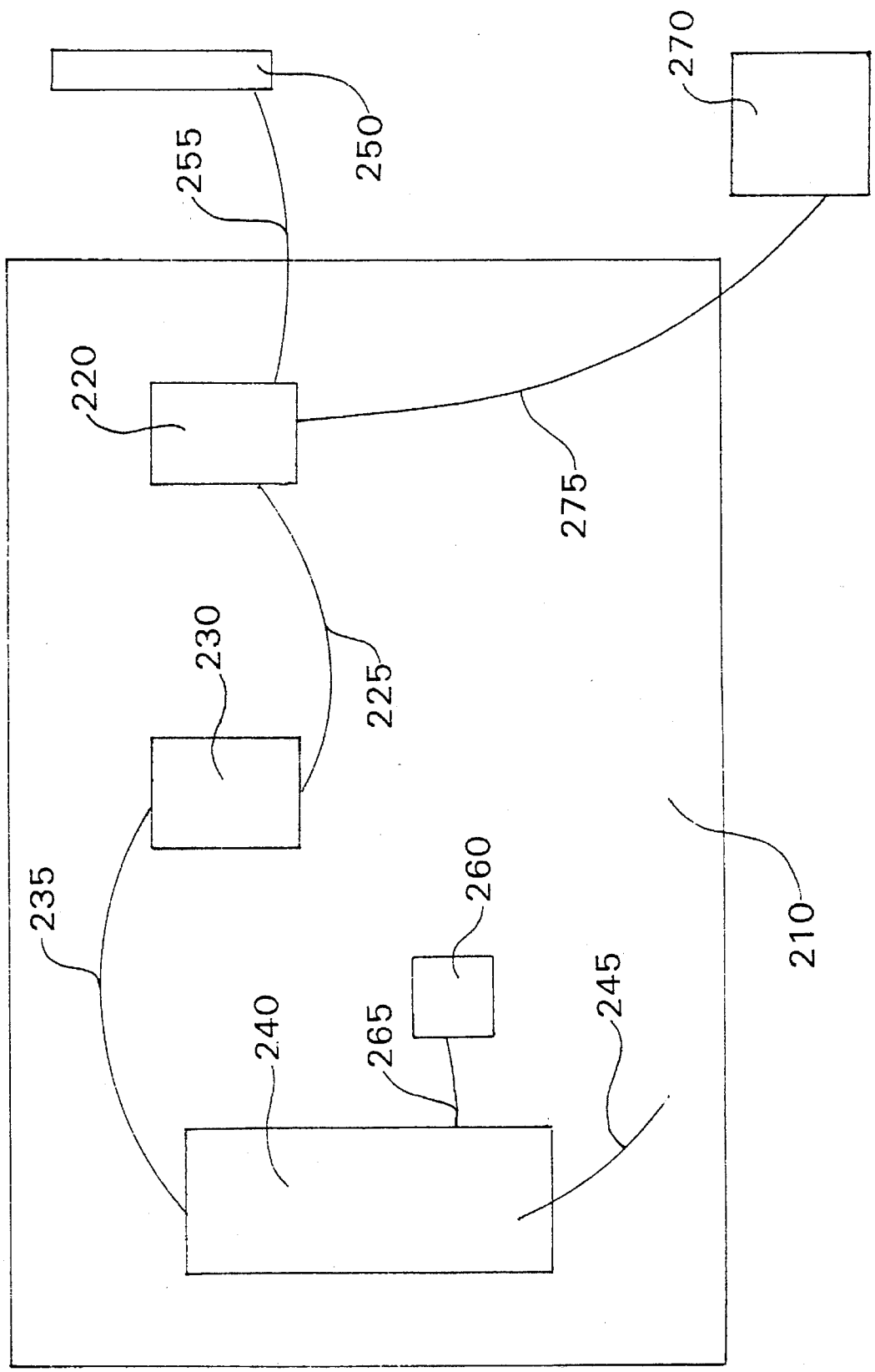
FIG. 2 is a diagram of the inside view of the front panel of case 10 of FIG. 1 showing the time and speed controls for the motor.

As seen in FIG. 2, to the inside front panel 210 of the case is attached motor controller 240, preferably a DC motor controller comprising a rheostat with an on/off switch (not shown) for converting AC to DC. Controller 240 is connected by electrical connector 245 to motor 90 of FIG. 1. Controller 240 is also connected by electrical connection 235 to an AC relay 230, preferably also attached to the case, and preferably a 100 V AC relay with a remote on/off switch (not shown) accessible to the subject to allow shut-off of the device in case of emergency. Relay 230 is in turn connected by electrical connection 225 to mechanical timer 220, preferably also attached to the case, which controls the power to the device by means of an on/off switch. Preferably the timer is a 60-minute or 20-minute timer attachable by cord 275 to a 110 V AC receptacle 270 and having a control switch or knob (not shown) extending to the outside of front panel 220 for ease of operation. Timer 220 may also control sound source 250, to which it is connected by electrical connection 255, which provides suitable sounds, such as recorded choral tones, for enhancing trance induction.

Controller 240 may optionally be connected by electrical connection 265 to programmable speed and/or direction control means 260, e.g. embodied in a computer chipboard, to vary the speed and direction of rotation of the platform 20 to enhance or change the quality of the subject's experience.

The foregoing components are sized and powered so as to automatically provide a rotational speed sufficient to induce the desired trance or relaxed state without causing unpleasant side effects, preferably between about 10 and about 60 revolutions per minute, and more preferably between about 15 and about 30 revolutions per minute. It has been found that speeds in excess of about 60 revolutions per minute cause nausea in a significant number of subjects. Once the subject is lying on the rotating platform and trance induction has been begun or the trance state has occurred, it will be difficult for the subject to manually control the speed of rotation to slow it down if the subject is experiencing nausea, or even to signal an operator to do so. Side effects from too-fast rotation include nausea, vomiting, and visionary experiences indicative of illness which can block out and interfere with the subject's ability to obtain other information from non-ordinary reality as a result of his trance state.

Figure 3:
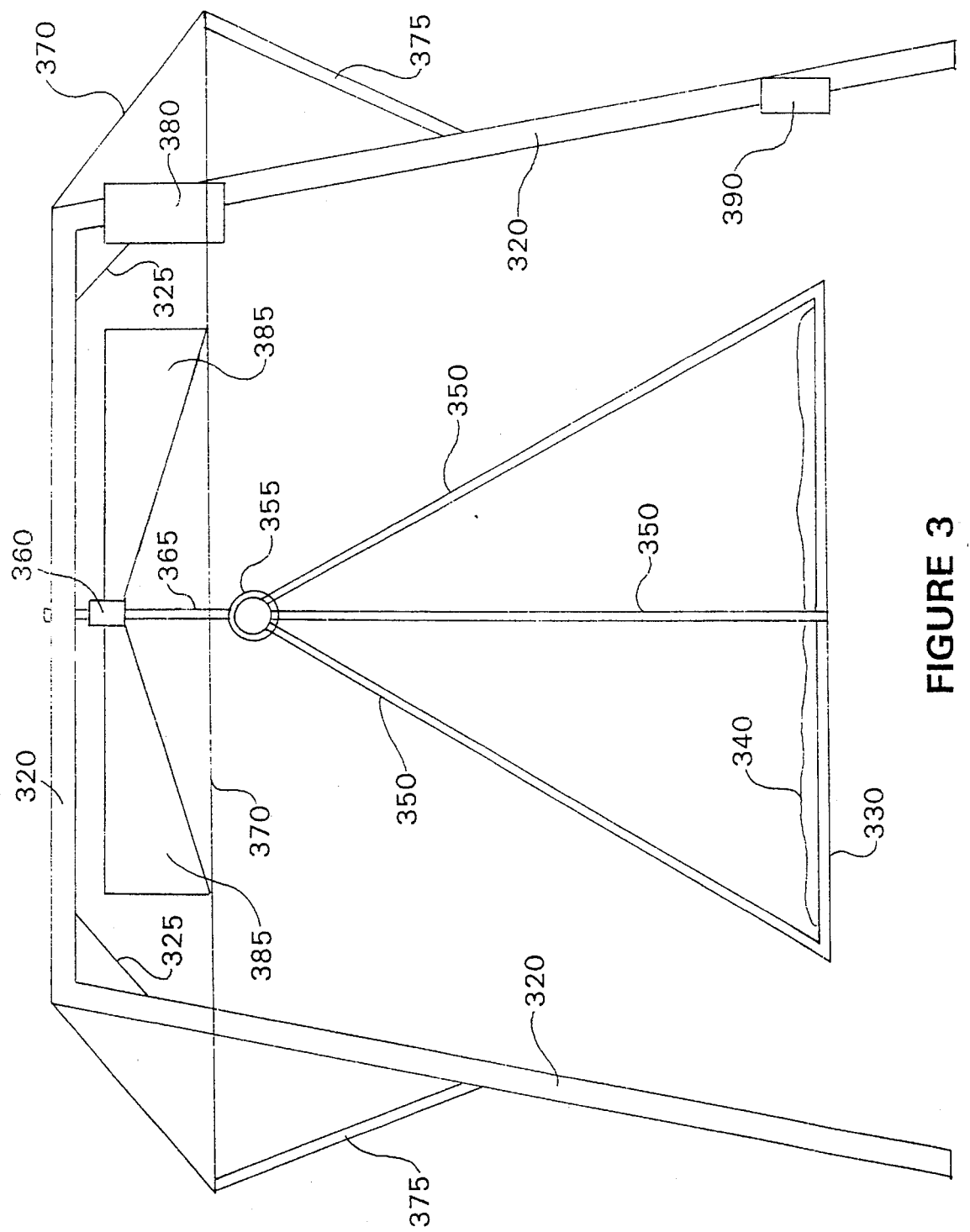
FIG. 3 is a diagram to scale of another embodiment of this invention wherein the subject lies on a platform suspended on ropes connected to an overhead point and rotated from the top by means of an automatically controlled motor.

FIG. 3 shows a further embodiment of this invention. In this embodiment, a platform comprising a rigid non-bending frame 330, e.g. of aluminum tubing depicted as 7" in height, in which a body support 340, e.g. a fabric hammock about 78 inches long, or other suitable length for supporting an adult human body, is provided, suspended on ropes, cords, straps, or rigid rods 350, preferably nylon webbing straps, to attachment point 355 of a rigid rod 365. Attachment point 355 may be a knob, a carabiner threaded through rod 365, or other means of attachment known to the art. Rod or shaft 365 is attached to ball bearing swivel 360 powered by an AC fan motor 380 attached to frame 320. Fan vanes 385 may optionally be attached to ball bearing swivel 360. Preferably frame 320 is comprised of steel tubing. Fan motor 380 is attached to fan timer 390, and powered by a suitable power source, such as a 110 V AC receptacle. Optional awnings 370 may be attached to frame 320 supported by awning braces 375. Frame 320 may also be provided with corner braces 325 to provide strength and stability.

Figure 4:
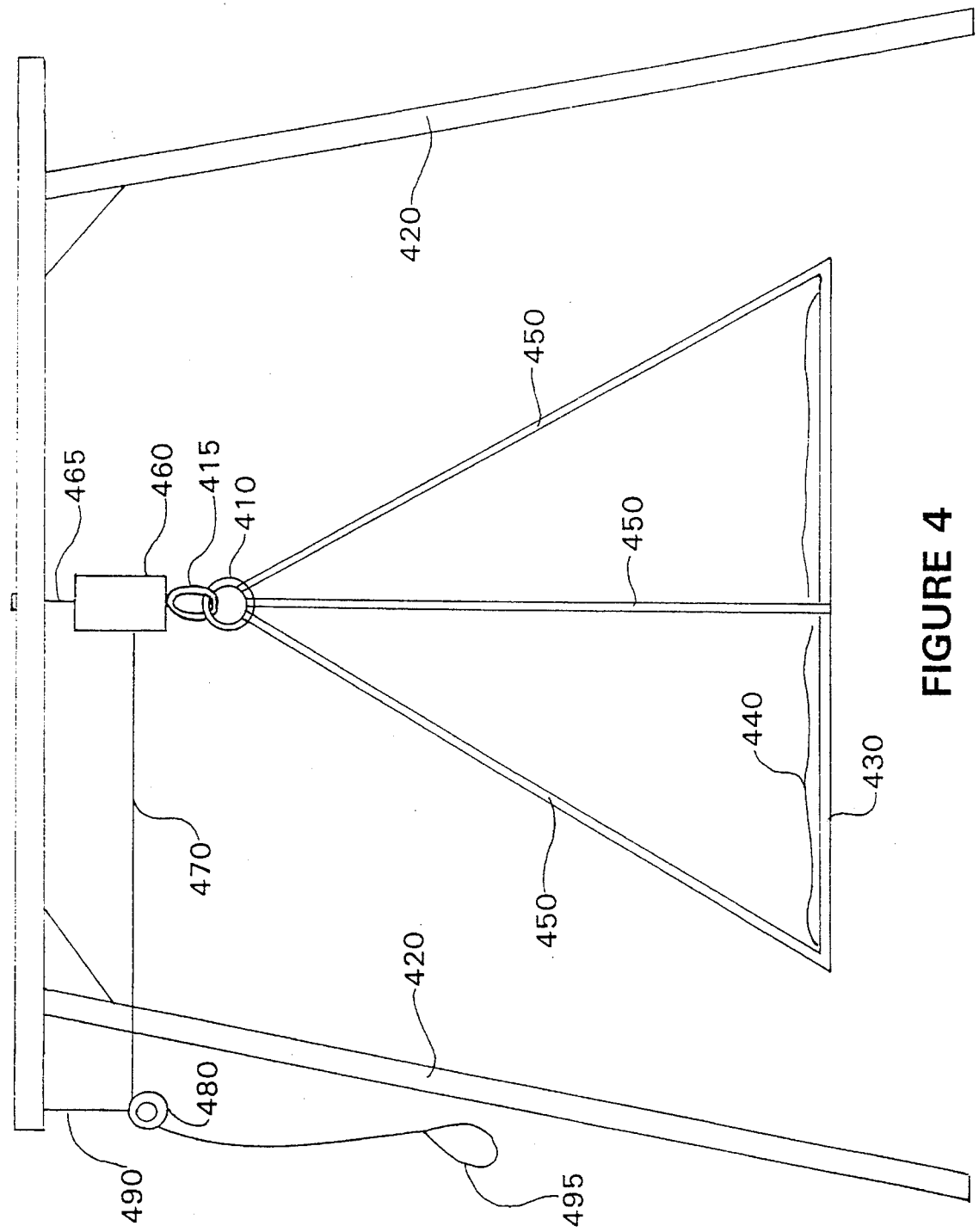
FIG. 4 depicts a manually-driven hanging embodiment of this invention involving winding and unwinding of the cords suspending the body support means from a central point, with rope and pulley means for maintaining the rotation.

FIG. 4 shows an embodiment of this invention in which body support means comprising a rigid skeleton 430, e.g. of aluminum tubing, in which a body support 440, e.g. a fabric hammock, is provided, suspended on ropes, cords, or straps 450, preferably nylon webbing straps, to a first ring or carabinier 410, in turn attached to a second ring or carabinier 415, attached to drum 460. Ring 415 may be fixedly attached to said drum or may be attached by means allowing for only limited rotation, such as by being threaded through a cord or bar spanning the horizontal underside of drum 460. Drum 460 is attached to frame 420, preferably by rotatable means such as a rope or strap 465. Drum 460 is fixedly attached to rope 470 which runs through pulley 480 affixed by attachment means, e.g. a second rope or chain 490, to the top of frame 420. Rope 470 hangs down from said pulley 480, to a point from which it may be conveniently pulled by an operator or a subject. Preferably rope 470 terminates with a handle 495. Optionally a weight (not shown) may be attached to the rope to help control the speed and momentum of rotation.

As will be appreciated by those skilled in the art, the device depicted and described in detail herein may be modified by means known to the art in various particulars without modifying its ability to function as a trance and relaxation-inducing device. The size and shape of the body support, means for rotating the support, frame or base, direction of rotation, and other aspects of the invention may be modified while still providing the basic platform having an automatically controlled speed of rotation sufficient to induce the trance or relaxed state without causing nausea. Because the device is designed for continuous usage by multiple subjects, it is preferred that the rotation be automatically controlled at the correct speed. It would be most preferred that no braking mechanisms be used. Such braking mechanisms are inefficient and cause waste of energy and build up of undesirable heat, as well as excessive wear on the motor, leading to greater likelihood of breakdown. It is also advisable that the motor be shielded so that its magnetic field does not affect the user. Such shielding means may comprise strategically placed magnets or other means known to the art.

In operation, the subject lies supine on platform 20 while it is not rotating and blocks out light from his eyes, preferably using light shield 130. The operator, which may be the subject, activates timer 220. Timer 220, operatively connected to AC relay 230 in turn activates DC motor control 240 through said relay 230 to cause rotation of second sheave 75. Second sheave 75 is connected to first sheave 70 by means of V-belt 80, and causes first sheave 70 to rotate at one-half the speed of second sheave 75. This rotation in turn causes shaft 50, to which first sheave 70 is fixedly attached, to rotate at the same speed, causing platform 20, to which it is fixedly attached through flange 40 and plate 30, to rotate horizontally at the same speed causing platform 20 to begin slowly rotating, preferably in a clockwise direction at a speed fast enough to induce trance or relaxation but not so fast as to cause nausea or other unpleasant side effects, preferably between about 10 and about 60 revolutions per minute. While the subject rotates, it is preferred that suitable sounds be generated from sound source 250 which may be a single speaker or multiple speakers placed at multiple points around the rotating platform. Choral sounds have been found to be effective in inducing the trance state. The platform rotates for period determined by said timer, at least about five minutes and up to about thirty minutes and preferably about fifteen to about twenty-five minutes, then automatically stops. The subject then removes the light shield 130 from his eyes and gets up. No unpleasant side effects should be felt.

As discussed above, the device may be programmably controlled such that the speed and direction of rotation is varied, such as by slowing gradually to a stop, then reversing direction one or more times during the period of operation.

In an embodiment utilizing the device shown in FIG. 3, the subject lies or sits in the body support means 330 supported by cords 350 attached to attachment point 355. Motor 380 is activated by timer 390 to turn a sufficient number of revolutions, preferably about 18, such that body support means 340 and 330 begin to slowly rotate. Because of the inertia of the system, the rotation of rod 365 and attachment part 355 causes the cords 350 to wind up about each other. When a sufficient, maximum allowable degree of winding has been achieved, the timer shuts off, and the body support decelerates and comes to a stop and begins to rotate in the opposite direction as the cords unwind, at a steadily increasing rate of speed not exceeding about 60 revolutions per minute, and preferably not exceeding about 30 revolutions per minute. When the cords are unwound, the rotation decelerates, stops and begins to accelerate in the opposite direction. The timer then activates the motor to continue the rotation, such that the maximum allowable winding is achieved, at which point the timer de-activates the motor and the cycle is repeated. The maximum allowable winding is set such that the speed of rotation does not exceed the desired values, and is preferably about 18 twists of the cords. The motor is preferably programmably controlled by the timer to turn between about 20 and about 30 revolutions when first activated, to be inactivated for a period of about two minutes to about three minutes, and to again begin rotation for between about 20 and about 30 revolutions followed by a second inactive period between about two minutes and about three minutes. The second cycle is repeated for up to 30 minutes as desired.

In a similar embodiment depicted in FIG. 4, manual rather than motorized means are used to maintain the rotation. The platform comprising skeleton 430 and fabric 440 in which the subject lies, is manually rotated to wind up cords 450 and cause rope 470 to wind around drum 460. The platform is then released and unwinds at a speed between about 10 and about 60 rpm, and when completely unwound, begins to wind in the opposite direction under its own momentum. When it has exhausted its momentum, it slows, comes to a stop, and begins to unwind in the opposite direction. An operator or the subject may provide additional momentum to compensate for slowing due to friction by pulling on the end of rope 480, preferably by means of handle 495, at a time when the rope is wound around spool 460 in a direction such that its unwinding would enhance the rotation then occurring. As will be readily appreciated, pulling the rope at a time when its unwinding will cause the drum to rotate in a direction opposite to the direction of the platform at that point will detract from the momentum of rotation. With a little practice and in accordance with the discussion above with respect to the embodiment of FIG. 3, the operator will understand how hard and at what point in time to pull the rope to maintain smooth rotation.

As will be appreciated by those skilled in the art, the drum may act as a means for controlling the speed of rotation to be less than about 60 rpm. Pulling the rope 465 at a time when it is winding will act to slow the rotation.

It has been found that a period of at least about five minutes is required for trance induction or effective relaxation. Periods up to thirty minutes may be utilized without adverse effects.

It has been found that subjects experience the sensation of being disconnected and free of their bodies; many report experiences of floating among the stars and planets. Visionary experiences are heightened, and a sense of heightened relaxation and well-being is felt.

What is claimed is:

1. A system for inducing a trance state in an adult subject comprising:

(a) horizontal rigid, non-bending body support means adapted to support said subject in a supine position during rotation of the device;

(b) rotating means operably connected to said body support means to horizontally rotate said body support means;

(c) speed control means operably connected to said rotating means to control the speed of said rotation to be between about 10 and about 60 revolutions per minute, (d) a light shield means worn by the subject during rotation of said body support means for blocking light from the subject's eyes.

2. The device of claim 1 also comprising timing means operably connected to said rotating means for timing the rotation of said body support means.

3. The device of claim 1 also comprising a sound source adjacent to said rotating body support means.

4. The device of claim 1 wherein said rotating means comprise a motor operably connected to a shaft affixed to the underside of said body support means.

5. The device of claim 1 wherein said rotating means comprise a motor operably connected to a shaft from which said body support means are suspended.

6. The device of claim 1 wherein said rotating means comprise a set of cords attached to and suspending said body support means capable of being wound about each other during use.

7. The device of claim 6 also comprising a rotatable drum from which said set of cords are suspended and a rope attached to said drum whereby said drum may be rotated during use by pulling said rope.

8. The device of claim 1 wherein said automatic speed control means comprise a rheostat operably connected to a motor of said rotating means.

9. The device of claim 1 wherein said rotating means are programmably connected to speed and direction control means whereby the speed of said rotation are varied and the direction of rotation reversed.

10. The device of claim 1 also comprising means for providing vertical motion of said body support means.

11. The device of claim 10 wherein a direction reversing means comprise a set of cords suspending said body support means from a central point, capable of winding up about each other during use when said body support means is rotated.

12. A system for inducing an altered state of consciousness in a subject comprising:
   (a) body support means not comprising a shaft extending upward from the center thereof, adapted to support an adult human body while rotating about a point in the center of the body support means,
   (b) rotating means operably connected to said body support means to horizontally rotate said body support means at a speed between about 10 and about 60 revolutions per minute,
   (c) means for reversing the direction of said rotation,
   (d) a light shield means worn by the subject during rotation of said body support means for blocking light from the subject's eyes.

13. The device of claim 12 wherein said direction-reversing means comprise programmed speed and direction control means operably connected to said rotating means.

14. A method for inducing a trance state in an adult subject comprising:
   (a) placing the subject supine on a horizontal, rigid, non-bending body support means not comprising a shaft extending upward from the center thereof;
   (b) activating rotating means to cause said body support means to rotate horizontally about a point in the center of the body support means at a speed between about 10 and about 60 revolutions per minute;
   (c) maintaining said rotation for a period between about five and about thirty minutes,
   (d) using a light shield means to block light from the subject eyes.

15. The method of claim 14 wherein the speed of rotation of said body support means is varied and the direction of rotation reversed.

16. The method of claim 14 wherein the body support means is also caused to move in a vertical direction.

17. A system for inducing a trance state in an adult subject comprising:
   (a) horizontal body support means adapted to support said subject in a supine position during rotation of the device;
   (b) rotating means operably connected to said body support means to horizontally rotate said body support means;
   (c) speed control means not comprising a brake operably connected to said rotating means to control the speed of said rotation to be between about 10 and about 60 revolutions per minute,
   (d) a light shield means worn by said subject during rotation of said body support means for blocking light from the subject's eyes.

18. A device for inducing a trance state in an adult subject comprising:
   (a) horizontal body support means comprising a platform suspended on ropes or cords connected to an overhead point, adapted to support said subject in a supine position during rotation of the device;
   (b) rotating means operably connected to said body support means to horizontally rotate said body support means;
   (c) speed control means operably connected to said rotating means to control the speed of said rotation to be between about 10 and about 60 revolutions per minute.

19. The device of claim 18 wherein said body support means comprise a hammock.

* * * * *